United States Patent [19]

Sfakianos et al.

[11] Patent Number: 5,443,474
[45] Date of Patent: Aug. 22, 1995

[54] MENISCECTOMY KNIFE

[75] Inventors: Peter Sfakianos, Shingle Springs, Calif.; Fredric L. Milder, Brookline, Mass.

[73] Assignee: Implemed, Inc., Brookline, Mass.

[21] Appl. No.: 207,363

[22] Filed: Mar. 7, 1994

[51] Int. Cl.⁶ .............................................. A61B 17/32
[52] U.S. Cl. ..................... 606/167; 606/170; 30/294
[58] Field of Search ............... 606/167, 170, 166, 171, 606/180; 30/272.1, 289, 294; 128/4-6

[56] References Cited

U.S. PATENT DOCUMENTS

| | | |
|---|---|---|
| 3,716,056 | 2/1973 | Brodsky et al. .................... 606/167 |
| 3,835,859 | 9/1974 | Roberts et al. . |
| 3,915,169 | 10/1975 | McGuire . |
| 4,006,746 | 2/1977 | Edwards . |
| 4,026,295 | 5/1977 | Lieberman . |
| 4,067,340 | 1/1978 | LeNoir . |
| 4,239,045 | 12/1980 | Schlein . |
| 4,473,076 | 9/1984 | Williams et al. . |
| 4,497,320 | 2/1985 | Nicholson et al. . |
| 4,520,815 | 6/1985 | Marinoff . |
| 4,580,563 | 4/1986 | Gross . |
| 4,600,005 | 7/1986 | Hendel . |
| 4,649,919 | 3/1987 | Thimsen et al. . |
| 4,674,500 | 6/1987 | DeSatnick . |
| 4,700,702 | 10/1987 | Nilsson . |
| 4,723,546 | 2/1988 | Zagorski . |
| 4,733,662 | 2/1988 | DeSatnick et al. . |
| 4,834,729 | 5/1989 | Sjostrom . |
| 4,983,179 | 1/1991 | Sjostrom . |
| 5,112,299 | 5/1992 | Pascaloff . |
| 5,122,152 | 6/1992 | Mull ........................................ 30/294 |
| 5,261,923 | 11/1993 | Soares ................................. 606/180 |
| 5,292,330 | 3/1994 | Shutt .................................... 606/167 |

FOREIGN PATENT DOCUMENTS

| | | | |
|---|---|---|---|
| 2737014 | 3/1979 | Germany ............................. 606/170 |
| 2161707 | 1/1986 | United Kingdom ................ 606/170 |

Primary Examiner—Stephen C. Pellegrino
Assistant Examiner—William Lewis
Attorney, Agent, or Firm—Lahive & Cockfield

[57] ABSTRACT

A meniscectomy knife includes a preformed cutting trace through which a cutting element moves in response to motion producing means disposed on a handle. The cutting trace defines an arc having a size and shape which closely correspond to the lines of stress along a meniscus in the meniscal region of a human knee joint.

29 Claims, 7 Drawing Sheets

MENISCECTOMY KNIFE

TECHNICAL FIELD

This invention relates to surgical instruments used in arthroscopic surgery. More particularly, it relates to surgical knives used to excise and remove torn meniscal tissue from a human knee joint.

BACKGROUND OF THE INVENTION

The human knee joint is a relatively complex articulation of several bones in the leg. It acts as a hinge between the femur (thigh bone) and the tibia (shin bone) and as a gliding articulation between the femur and the patella (knee cap). The articulating surfaces (condyles) of these bones are surrounded by various ligaments, tendons, and cartilage which cushion the bones in the joint and coordinate and guide their movements. Among the ligaments in the knee joint are the lateral and medial menisci. The menisci are approximately semicircular in shape and are posteriorly attached to the tibia, extend transversely to form an extension of the tibial condyles. The menisci are interconnected anteriorly by the transverse ligament.

The menisci are frequently torn or displaced as a result of the application of abnormal forces to either side of the knee. Because each meniscus is peripherally and posteriorly attached to the articulating surfaces of the knee joint, tears may occur anywhere along the perimeter and through the body of the meniscus. Meniscal tears generally extend longitudinally through the body of the meniscus, along lines of hoop stress extending parallel to the circumferential fibers of the tissue. Alternatively, they may extend radially from the inner edge of the meniscus toward the periphery. Meniscal tears may also be obliquely oriented from the inner edge through the body of the meniscus. A torn meniscus may jam or dislocate from between the condyles, causing the joint to lock. Accordingly, a meniscus which has been torn or loosened is generally at least partially excised and removed from the joint.

As opposed to "open" surgery, arthroscopic surgery of the knee involves the placement of several incisions, or portals, in the knee joint region for insertion of various instruments for viewing, grasping, cutting and irrigating tissue. Meniscectomy surgery, the removal of a meniscus or part of one, is generally performed using at least two, and frequently three, portals. One portal is used for insertion of various specialized grasping and/or cutting instruments. A second portal is often used for insertion of an irrigation cannula, and a third portal is often used for insertion of an arthroscope.

Various instruments have been designed to excise torn or damaged meniscal tissue from the knee joint. Meniscectomy instruments are generally highly specialized to grasp and/or cut tissue by shaving, snipping, twisting or nibbling. Some meniscectomy instruments are designed specifically for open surgery while others are designed specifically for arthroscopic surgery.

Some meniscectomy instruments of the prior art feature a guided cutting blade on a track which conforms to the interior of the knee cavity for more precise positioning of the blade. The track may be malleable or flexible to allow manual shaping of the path along which the cutting blade will travel in the guide. For example, U.S. Pat. No. 3,835,859 to Roberts et al. discloses an instrument for complete removal of a meniscus during open surgery having a sliding cutting blade mounted on a flexible guide which is conformed to the interior of the knee cavity by the surgeon. U.S. Pat. No. 3,915,169 to McGuire discloses a surgical knife for removing a meniscus arthroscopically which includes a malleable shank with a blade attached at a distal end thereof. The malleable shank may be manually shaped by the surgeon prior to and during surgery to more precisely position the blade within the incision. In this case, the knife shank is also guided during the procedure by the tissues surrounding the knee joint.

Other meniscectomy instruments may feature a fixed cutting blade track in which a flexible cutting blade is mounted. U.S. Pat. No. 4,067,340 to Le Noir discloses a meniscectomy instrument for open surgery having grooved blade guides formed in the shape of the periphery of the meniscus. The blade guides are located on separate handles which are inserted separately into the open joint and thereafter joined with a cutting blade frame which holds a flexible cutting blade. The cutting blade is held between the grooved blade guides and advances along them, permitting excision of the meniscus along a path described by the grooved guides.

Still other meniscectomy knives may feature multiple cutting blades which are located in precise relationship to one another. U.S. Pat. No. 4,239,045 to Schlein discloses a meniscectomy knife for performing a complete meniscectomy which has two cutting blades fixed at right angles to one another with a guide member located at the intersection of the blades to facilitate insertion and manipulation of the knife. The instrument is curved to conform to the outer shape of the meniscus and has a cutting edge at its forward end. The inner blade also has a cutting edge at its forward end, such that the forward end of the knife presents two cutting edges perpendicularly joined at a common edge.

Meniscectomy knives which are highly specialized for a particular task may require the simultaneous use of additional instruments during meniscectomy surgery, thereby necessitating an increase in the use and number of portals and/or greater involvement by the surgical team. Even meniscectomy knives which have a flexible cutting guide designed for shaping by the surgeon prior to or during surgery may be problematic. It is difficult for the surgeon to anticipate accurately an optimum shape for the cutting guide once the knife is inside the patient. Furthermore, manipulation of a flexible cutting guide during surgery is difficult and cumbersome and may result in a misshapen cutting guide and imperfect excisions of the meniscal tissue. A shaped cutting guide may also change its shape during the surgery as a result of forces exerted upon it during manipulation of the knife within the patient. Furthermore, prior art meniscectomy knives which have a shaped cutting guide and flexible blades, such as the Le Noir knife, or multiple cutting blades, such as the Schlein knife, are also difficult to position precisely within the patient. Neither the flexibility of the cutting blades nor the configuration of the cutting blades on such knives assists the surgeon in placing the instrument within the knee joint at the precise location required for effective excision of any portion of the meniscus.

It is therefore an object of this invention to provide an improved surgical knife useful in excising torn or damaged meniscal tissue from a human knee joint. It is another object of the invention to provide a meniscectomy knife which is anatomically shaped to precisely surround and excise some portion of the meniscus along its circumferential fibers and thus parallel to the lines of greatest stress therein without damaging surrounding nerves, cartilage, blood vessels or ligaments. It is another object of the invention to provide a meniscectomy knife which provides a guided path for excision of portions of the meniscus. It is another object of the invention to provide a meniscectomy knife which may be used with greater versatility in meniscectomy surgery than the prior art instruments, with the objective of minimizing the number of portals required, the types of meniscectomy instruments used, and the extent of surgical team support required. It is another object of the invention to provide a meniscectomy knife which may be easily inserted into and manipulated inside a patient with minimum discomfort or trauma to the patient.

SUMMARY OF THE INVENTION

These and other objects of the invention may be accomplished, according to one aspect of the invention, with a meniscectomy knife which comprises a handle having distal and proximal ends and a handle axis, and a hollow guide tube affixed to the distal end of the handle and extending away from the handle along the handle axis. At least a portion of the guide tube is preformed to include an arc portion defined by a cutting radius, the arc portion having a first surface and a slot extending along at least a portion thereof to define a cutting trace therein. An actuating wire is disposed within the guide tube and movable therethrough along a longitudinal axis thereof. Motion producing means are disposed within the handle for imparting longitudinal motion to the actuating wire along its longitudinal axis. A proximal end of the actuating wire is affixed to the motion producing means such that activation of the motion producing means causes longitudinal movement of the actuating wire along the wire axis within the guide tube. A distal end of the actuating wire moves correspondingly along an arcuate path defined by the arc portion of the guide tube. A cutting element is affixed to the distal end of the actuating wire and extends through the slot in the arc portion of the guide tube and is movable along the cutting trace in the arc portion of the guide tube.

According to another aspect of the invention, there is provided a meniscectomy knife which comprises a hollow handle having distal and proximal ends and a handle axis, with a retractable plunger disposed within the handle and movable therein along the handle axis. A guide tube is affixed to the distal end of the handle and extends away from the handle along the handle axis. At least a portion of the guide tube is preformed to include an arc portion defined by a cutting radius. The arc portion has a first surface and a slot extending along at least a portion thereof to define a cutting trace therein. An actuating wire is disposed within the guide tube and movable therethrough along a longitudinal axis thereof. A proximal end of the actuating wire is affixed to the distal end of the retractable plunger such that movement of the plunger along the handle axis causes longitudinal movement of the actuating wire along the wire axis within the guide tube and corresponding arcuate motion of a distal end of the actuating wire in the arc portion of the guide tube. A cutting element is affixed to the distal end of the actuating wire and extends through the slot in the arc portion of the guide tube and is movable along the cutting trace.

According to another aspect of the invention, there is provided a meniscectomy knife which comprises a hollow handle having distal and proximal ends and a handle axis, and a guide tube which is affixed to the distal end of the handle and extends away from the handle along the handle axis. At least a portion of the guide tube is optionally preformed to include an offset portion defined by an offset distance from the handle axis and an arc portion defined by a cutting radius. The arc portion has a first surface and a slot which extends along at least a portion thereof to define a cutting trace therein. An actuating wire is disposed within the guide tube and movable therethrough along a longitudinal axis thereof. Motion producing means are disposed within the handle for imparting longitudinal motion to the actuating wire along the wire axis within the guide tube. A proximal end of the actuating wire is affixed to the motion producing means such that activation of the motion producing means causes longitudinal movement of the actuating wire along the wire axis within the guide tube and corresponding arcuate movement of a distal end of the actuating wire in the arc portion of the guide tube. A cutting element is affixed to the distal end of the actuating wire and extends through the slot in the arc portion of the guide tube and is movable along the cutting trace.

According to another aspect of the invention, there is provided a meniscectomy knife which comprises a hollow handle having distal and proximal ends and a handle axis, and a retractable plunger disposed within the handle and movable therein along the handle axis. A guide tube is affixed to the distal end of the handle and extends away from the handle along the handle axis. At least a portion of the guide tube is optionally preformed to include an offset portion defined by an offset distance from the handle axis and an arc portion defined by a cutting radius. The arc portion has a first surface and a slot extending along at least a portion thereof to define a cutting trace therein. An actuating wire is disposed within the guide tube and movable therethrough along a longitudinal axis thereof. A proximal end of the actuating wire is affixed to the distal end of the retractable plunger such that movement of the plunger along the handle axis causes longitudinal movement of the actuating wire along the wire axis within the guide tube and corresponding arcuate motion of a distal end of the actuating wire in the arc portion of the guide tube. A cutting element is affixed to the distal end of the actuating wire and extends through the slot in the arc portion of the guide tube and is movable along the cutting trace.

According to another aspect of the invention, there is provided a meniscectomy knife for use with a handle having a handle actuating member, comprising a guide tube for affixing to the distal end of the handle, at least a portion of the guide tube being preformed to include an arc portion defined by a cutting radius. The arc portion has a first surface and a slot extending along at least a portion thereof to define a cutting trace therein. An actuating wire is disposed within the guide tube and movable therethrough along a longitudinal axis thereof for affixing to the handle actuating member at a proximal end of the actuating wire, such that activation of the handle actuating member causes longitudinal movement of the actuating wire within the guide wire tube along the actuating wire axis. In response to such activation, a distal end of the actuating wire moves along the arcuate path defined by the arc portion of the guide tube. A cutting element is affixed to the distal end of the actuating wire and extends through the slot in the arc portion of the guide tube and is movable along the cutting trace. In a preferred embodiment, at least a portion of the guide tube is preformed to include an offset portion defined by an offset distance from the longitudinal axis.

In a preferred embodiment, the meniscectomy knife of the present invention includes motion producing means which can be, for example, a retractable plunger disposed within the handle and freely movable therein along the handle axis. The motion producing means may further include various mechanisms, such as ratchet or worm gear advancing mechanisms, to impart forward or backward motion to the retractable plunger.

The meniscectomy knife of the present invention may further include, as part of the cutting element, a broadened flat skid which extends from an exposed surface of the cutting element in a plane transverse to the plane of the cutting zone and parallel to the plane of the cutting trace in the arc portion of the guide tube. While the meniscectomy knife is inside a patient, the skid contacts and glides over or under surrounding tissue, particularly adjacent cartilage, during the cutting procedure, thereby protecting the surrounding tissue from contact with the cutting zone of the cutting element and facilitating correct and accurate placement of the knife in the meniscal region.

The meniscectomy knife of the present invention may further include a protective sheath affixed to the distal end of the guide tube adjacent to and distal to the cutting trace in the arc portion of the guide tube. The protective sheath forms a housing to prevent contact between the cutting zone of the cutting element and the surrounding tissue which might otherwise be exposed to the cutting element upon insertion and manipulation of the meniscectomy knife in the patient.

These and other features of the invention will be more fully appreciated with reference to the following detailed description which is to be read in conjunction with the attached drawings.

DETAILED DESCRIPTION OF THE INVENTION

The invention provides for a meniscectomy knife which provides a guided path through which a cutting element moves. The guided path has an arcuate shape of predetermined dimensions which closely correspond to the anatomy of the meniscal region of a human knee joint. The anatomical design of the meniscectomy knife ensures that the arcuate portion of the knife seats properly in the knee joint so that the cutting trace, which defines the path of the cutting element, is precisely located within the periphery of the meniscus.

As shown in FIGS. 1–3 and 6, the meniscectomy knife 10 includes a hollow handle 12 adapted to receive motion producing means 50, shown in the figures as a retractable plunger, at a proximal end 12a of the handle. The motion producing means 50 is movable along a longitudinal handle axis 16. A guide tube 20 extends longitudinally from a distal end 12b of the handle away from the motion producing means. A distal portion of the guide tube is preformed into an arc 22 with dimensions which closely correspond to the shape and size of the meniscus in the knee joint. The arc 22 includes a slot 24 extending along a first surface of the arc to define a cutting trace 26. An actuating wire 30 is disposed within the guide tube 20 and attached to the distal end 50b of the motion producing means 50 to be movable longitudinally through the guide tube 20. The longitudinal motion caused by motion producing means 50 translates to longitudinal movement of the actuating wire 30 within the guide tube resulting in arcuate motion of a distal end 30b of the actuating wire 30 along the arcuate path defined by the arc 22 of the guide tube 20. A cutting element 40 is affixed to the distal end 30b of the guide wire 30 and extends through the slot 24 in the arc 22 to be freely movable along the cutting trace 26.

The handle 12 is constructed as a hollow tube with a bore of sufficient diameter to permit movable engagement of the motion producing means 50, such as a plunger 50, therein. The length and diameter of the handle may be of any dimensions which permit the surgeon to easily and conveniently grasp, hold and manipulate the knife. A preferred handle length is approximately 5 inches, with a preferred handle diameter of approximately 0.75 inch.

The handle is preferably made of a rigid, lightweight, inexpensive and easily machinable or injection moldable material, such as a polymeric material, for example, polycarbonate or ABS. The proximal end 12a of the handle may be flanged for ease in grasping or manipulating the knife. A narrow bore may be located at the distal end 12b of the handle in which a proximal end 20a of the guide tube 20 is received and secured.

The handle 12, motion producing means 50, guide tube 20, actuating wire 30 and cutting element 40 may comprise an integral assembly such that the entire meniscectomy knife may be discarded after a single use. Alternatively, the handle 12 and motion producing means 50 may be detachable from the guide tube, actuating wire and cutting element, which themselves may be disposable or interchangeable with other elements or embodiments of the meniscectomy knife.

The motion producing means 50 is constructed as a plunger having a hollow shaft having an outer diameter which permits it to fit within and movably engage with the handle 12 along the handle axis 16. It is preferably made of a lightweight, rigid, inexpensive material which is similar to that used for the handle. The distal end 50b of the motion producing means includes a bore in which actuating wire 30 engageably and removably fits and preferably includes means for securing the proximal end 30a of the actuating wire thereto. The proximal end 50a of the plunger may be flanged or flared to facilitate grasping and manipulation of the motion producing means by the surgeon and to ensure that the plunger does not overextend into the bore of the handle.

Figure 1:
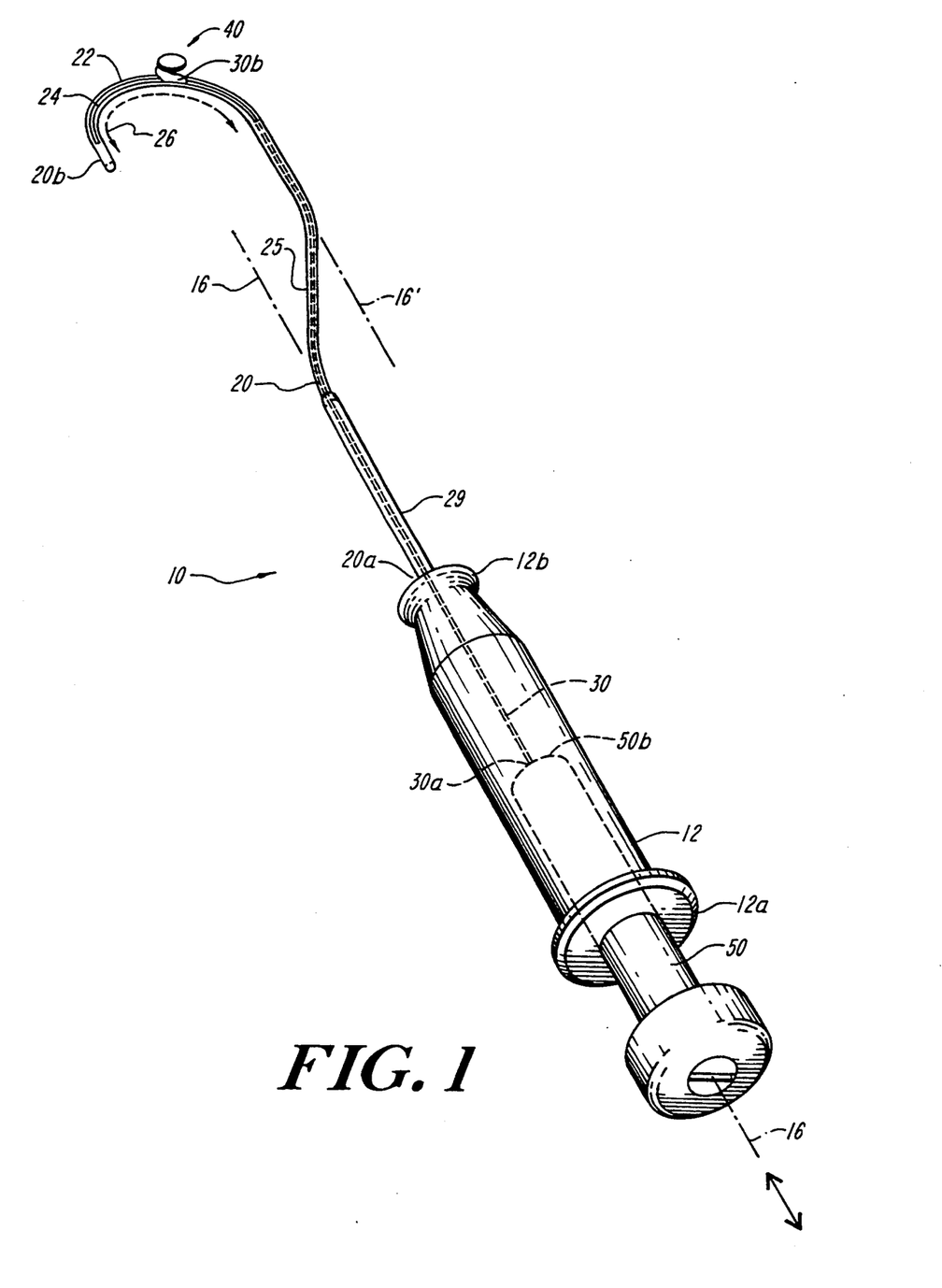
FIG. 1 is a perspective view of a meniscectomy knife according to the present invention.
Figure 2:
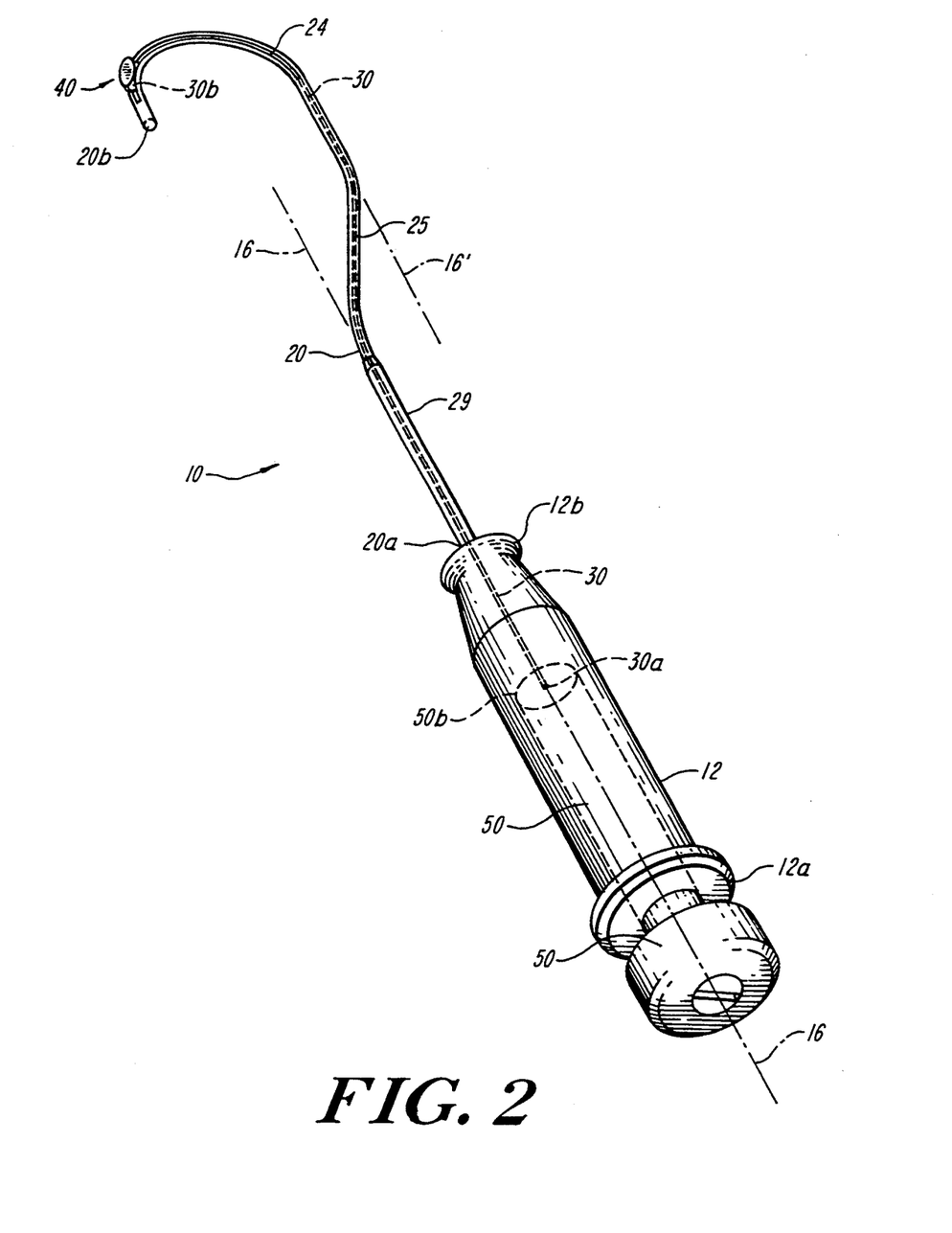
FIG. 2 is a perspective view of the meniscectomy knife in which the motion producing means is depicted as a retractable plunger which is fully extended into the handle, thereby positioning the cutting element at the distal end of the cutting trace.
Figure 3:
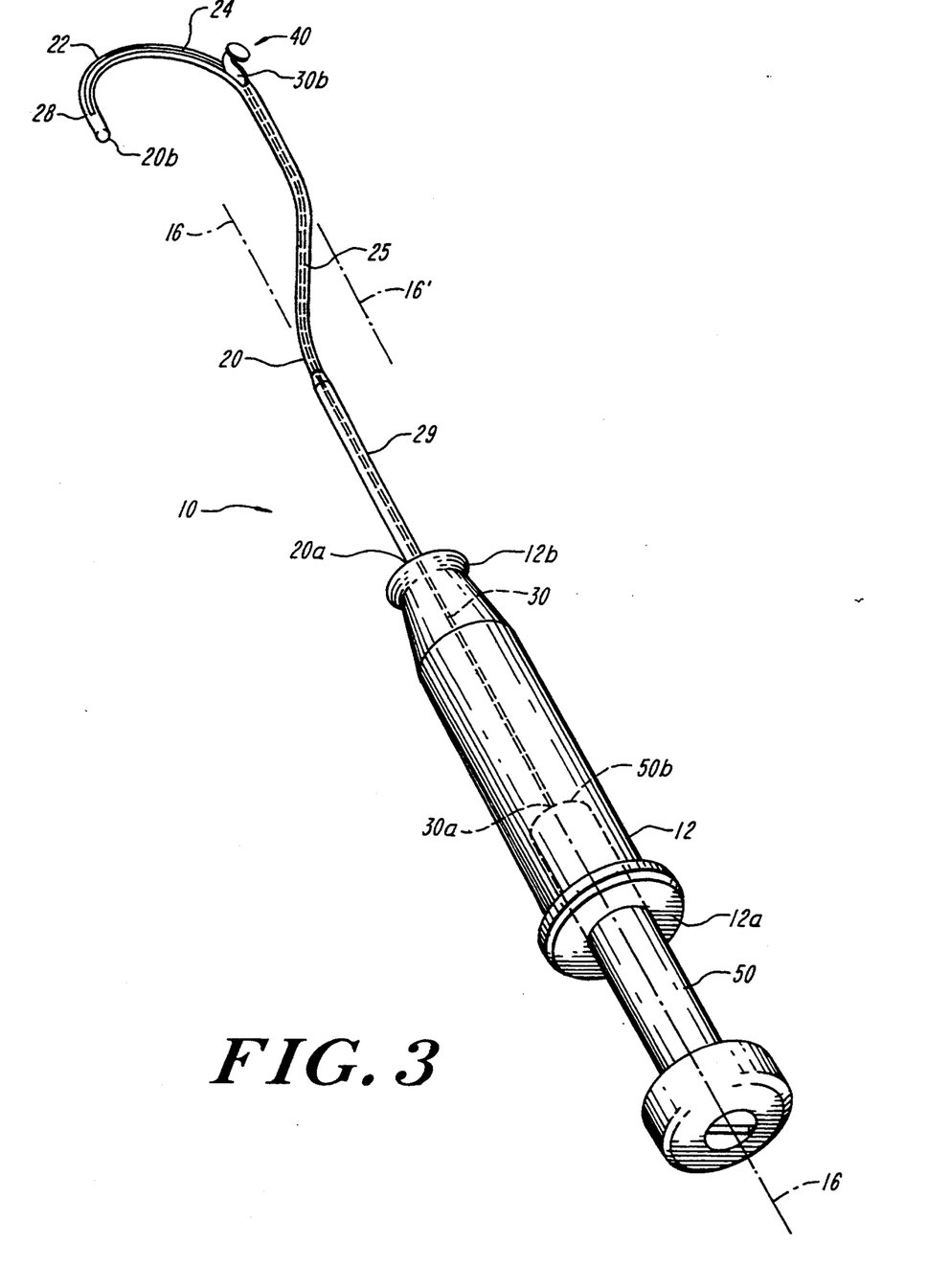
FIG. 3 is a perspective view of the meniscectomy knife with a retractable plunger which is fully retracted from the handle, thereby positioning the cutting element at the proximal end of the cutting trace.

As shown in FIG. 2, extension of the plunger into the handle 12 will cause the actuating wire 30 and cutting element 40 affixed to the wire to move to the distal end of the cutting trace 26. Conversely, as shown in FIG. 3, retraction of the plunger from the handle results in movement of the actuating wire and the cutting element affixed to the wire to the proximal end of the cutting trace. Extension and retraction of the plunger in a left-hand meniscectomy knife, illustrated in FIG. 6, causes the cutting element to move in a rotationally opposite direction from that, shown in FIGS. 1–3.

The guide tube 20 is a hollow shaft which extends longitudinally away from the distal end 12b of the handle 12 and is preferably formed over at least a portion of its length into a size and shape which closely corresponds to the interior anatomy of the meniscal region of the knee joint. It is preferably no greater than approximately 0.1 inch in outer diameter to facilitate its bending and shaping to the desired configuration. It is preferably constructed of a relatively rigid, smooth, durable material which is suitable for use in surgical environments, such as stainless steel, nickel or titanium. A reinforcing tube sleeve 29 may be located over a proximal portion of the guide tube 20 which is adjacent to and extends longitudinally away from the distal end 12b of the handle 12 to reinforce and strengthen the guide tube 20 at its point of emergence from the handle.

The bore of the guide tube 20 need only be sufficiently large to permit the free longitudinal movement of the actuating wire 30 therethrough.

A distal portion of the guide tube 20 is formed into the shape of an arc of a size which closely parallels the inner arcuate shape of the meniscus. Because of variations in the size of the human knee joint and in the size and location of the menisci therein, a range of meniscectomy knives according to the present invention, each with a guide tube having a slightly different arc size, is preferred. It is believed that three or four meniscectomy knives of the present invention, with arc radii differing by 0.25 inch from the largest to the smallest, will provide a sufficient range of sizes to ensure a precise matching of the size of the arc portion of the knife with meniscal regions in virtually any human knee joint.

The arc portion 22 of the guide tube 20 includes a slot 24 on a first surface thereof. Although the slot is preferably located on a top surface of the arc portion of the guide tube, it may be located on other surfaces of the guide tube as well, according to the desired cutting element design and the desired location of the cutting trace. The length of the slot 24 in the arc portion 22, which is determined by the length of a desired cutting arc, determines the length of the cutting trace 26 through which the cutting element 40 moves. The length of the slot also determines, for a given arc length and cutting radius, the distance through which the motion producing means 50 must move to cause longitudinal movement of the guide wire 30 through the guide wire tube 20 and corresponding arcuate movement of the cutting element 40 through the cutting trace 26.

The slot 24 is preferably sufficiently wide to permit the free movement therein of the cutting element 40 without friction or impedance. The slot is preferably not wider than the diameter of the actuating wire so that the actuating wire does not protrude through the slot. A preferred slot width is 0.030 inch.

The cutting element 40 moves precisely within the cutting trace 26 along the arcuate path defined by the arc portion of the guide tube in either a clockwise or counter-clockwise direction in response to longitudinal movement of the motion producing means 50 and actuating wire 30 affixed thereto. The cutting element 40 may be moved along the cutting trace 26 through the full arcuate path of the cutting trace, or through only a portion thereof. It may be moved through the cutting trace in increments, or it may be moved alternately back and forth in a rocking or sawing manner within the cutting trace. The path of the cutting element within the cutting trace is thus precisely defined by the arc portion 22 of the guide tube 20 and the location of the slot 24 therein, while the manner in which the cutting element is moved is determined and controlled by the motion producing means disposed within the handle of the knife.

The arcuate path of the cutting trace may extend over a relatively wide angular range, from 90° to 230°, with a preferred arc range of between 120° and 180°. The motion producing means 50 in the handle 12 causes movement of the actuating wire 30 in a longitudinal direction which is proportional to the arcuate distance through which the cutting element 40 moves in the cutting trace 26. The length of the arcuate cutting trace is approximately one-half to two inches and is preferably about one and one-half inches long.

The guide tube 20 may additionally contain an optional preformed offset portion 25 defined by an offset distance to the right or left of the handle axis 16 and located proximal to the arc portion 22 of the guide tube 20. The offset portion 25 of the guide tube 20 extends longitudinally from the distal end 12b of the handle and is thereafter offset a predetermined distance to either the right or the left from the handle axis 16. The offset portion of the guide tube is located between the distal end of the tube sleeve 29 and the proximal end of the arc portion 22 of the guide tube. As shown in FIGS. 1–3 and 6, the offset portion 25 is characterized by a diagonal extension of the guide tube 20 from the handle axis 16 to an offset axis 16' which is parallel to and offset from the handle axis by a distance which is determined by the size and shape of the meniscal region for which the knife is intended to be used.

A preferred meniscectomy knife as shown in FIGS. 1–3 and 6 has a cutting radius of between approximately 0.25 inch and 0.75 inch and preferably is approximately 0.5 inch. The offset axis 16' is displaced from the handle axis 16 by approximately 0.25 inch to 0.70 inch and preferably by approximately 0.5 inch.

Figure 6:
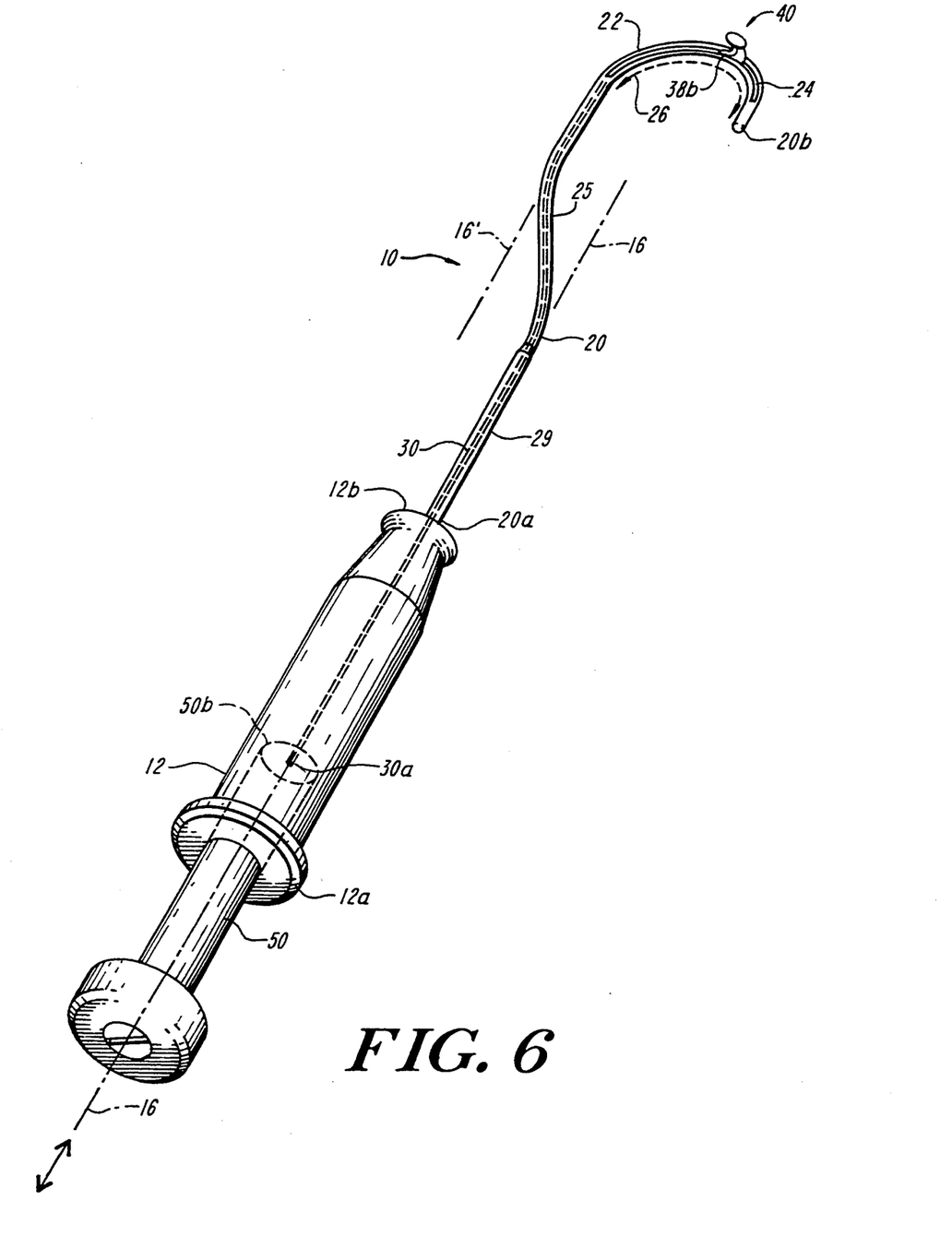
FIG. 6 is a perspective view of a left-hand meniscectomy knife according to the present invention.

In one preferred embodiment, a "right-hand" meniscectomy knife, shown in FIGS. 1–3, features a guide tube 20 having an offset portion 25 extending to the right of the handle axis 16. The cutting element 40 travels in a clockwise direction upon retraction of the motion producing means from the handle 12 and in a counter-clockwise direction upon extension of the motion producing means into the handle. In another embodiment, a "left-hand" meniscectomy knife, shown in FIG. 6, is the reverse of the right-hand knife: its offset portion extends to the left of the handle axis, and the cutting element travels in a counter-clockwise direction upon retraction of the motion producing means from the handle and in a clockwise direction upon extension of the motion producing means into the handle. Both embodiments of the meniscectomy knife are desirable to facilitate insertion of the knife through a standard single arthroscopic portal and to enable precise placement of the knife within the meniscal region for excision of any portion of the meniscus.

The actuating wire 30 extends through the guide tube 20 from a distal end 50b of the motion producing means 50. A cutting element 40 is affixed to a distal end 30b of the actuating wire 30 such that the cutting element 40 extends through the slot 24 in the arc portion 22 of the guide tube 20. The actuating wire 30 may be permanently or detachably secured to the distal end 50b of the motion producing means 50 and is freely movable along a longitudinal axis of the guide tube 20 in response to movement caused by the motion producing means.

The actuating wire 30 is preferably made of a strong, lightweight material which is suitable for use in surgical environments. It is preferably a wire or cable of sufficiently heavy gauge, such as, for example, 0.040 inch in diameter or greater, with sufficient rigidity to be movable in a longitudinal direction in response to applied axial or longitudinal force from the motion producing means without folding or bending within the guide tube. It is also preferably a material to which the cutting element 40 can be securely fastened, such as by welding. A preferred material for the guide wire include stainless steel and other corrosion resistant materials.

Figures 7, 8:
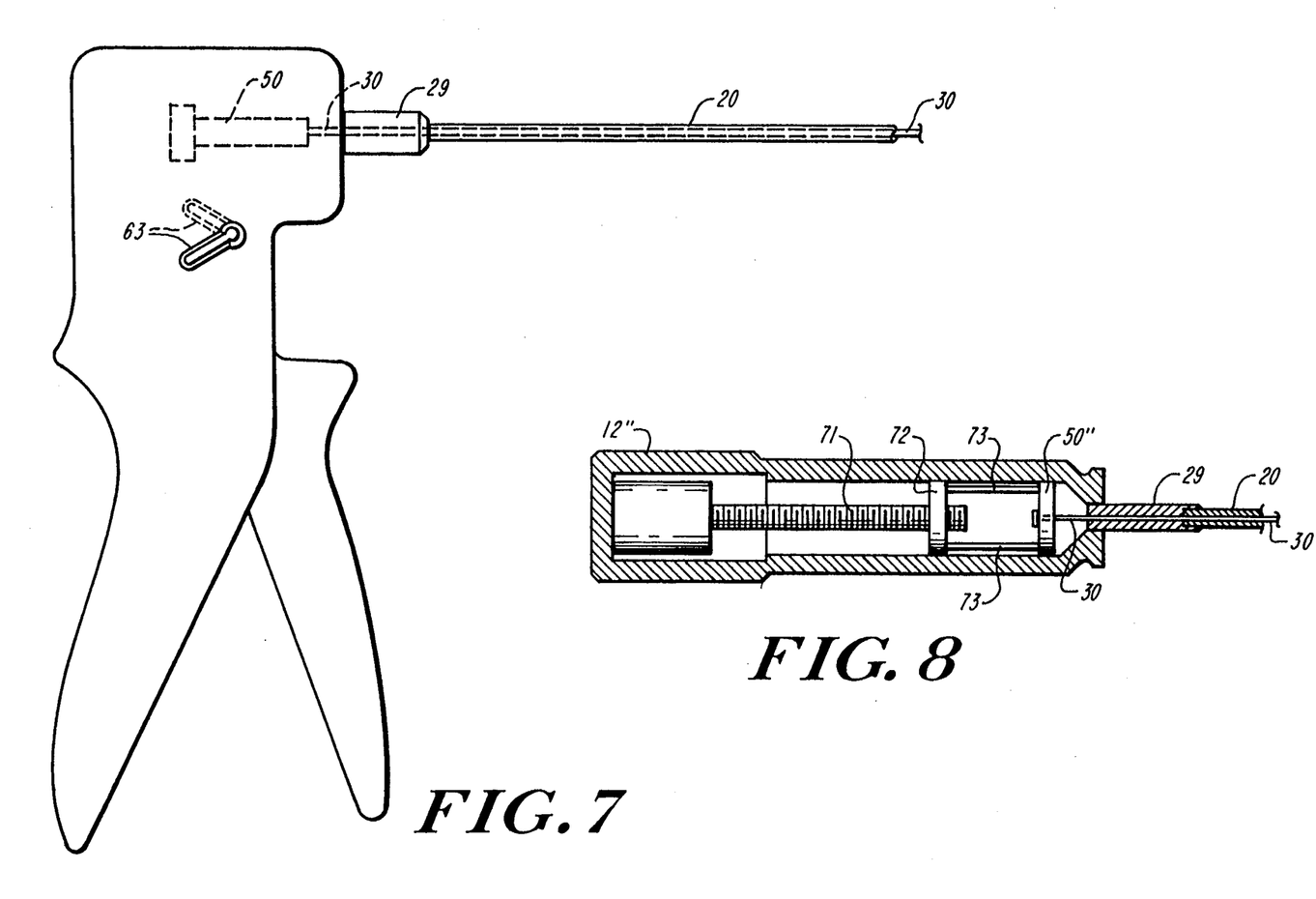
FIG. 7 is a perspective view of the meniscectomy knife having an alternative motion producing means in the form of a reversible rotating squeeze handle.
FIG. 8 is a longitudinal cutaway view of the meniscectomy knife having an alternative motion producing means in the form of an electrically driven ball screw mechanism.

The handle 12 is equipped with motion producing means 50, such as the retractable plunger depicted in FIGS. 1-3 and 6, for imparting longitudinal motion to the actuating wire 30 and the cutting element 40 affixed thereto. The motion producing means 50 may include, for example, a reversible direction electric motor and gear mechanism which permits controlled movement of the actuating wire and cutting element affixed thereto in either the forward or reverse direction. Alternatively, the motion producing means may be a reversible ratchet mechanism which permits controlled incremental movement of the actuating wire and cutting element with or without locking engagement of the actuating wire and cutting element at each incremental stop. As shown in FIG. 7, the handle 12' may be formed in a "squeeze-gun" configuration with the motion producing means 50', such as a plunger, totally enclosed within the handle. A lever 63, when moved from one position to another, changes the direction of plunger travel. Such mechanisms are known in the art.

Alternatively, the motion producing means could be a screw, rack and pinion, or worm gear mechanism which advances and/or retracts the actuating wire and cutting element by a predetermined distance with each rotation of the gear. FIG. 8 depicts a screw configuration wherein motion producing means 50" in the form of a short plunger is rigidly connected via rods 73 to a nut 72 which is restrained from rotating within the handle 12". A rotation producing means 70, such as a reversible electric motor, causes screw 71 to move reversibly and rotationally. When the motor is activated, the screw 71 turns, producing longitudinal motion of the nut 72 and of the plunger 50" thereby. Mechanisms such as the ratchet handle or screw gear handle could permit single-handed operation of the meniscectomy knife. The motion producing means may be controlled manually or by other means, such as electrically, pneumatically, or hydraulically.

Longitudinal motion imparted to the actuating wire 30 by the motion producing means 50 becomes arcuate motion of the cutting element 40 in the cutting trace 26. The distance of longitudinal travel of the actuating wire in response to the activation of the motion producing means is proportional to the arcuate distance traveled by the cutting element.

Figure 4A:
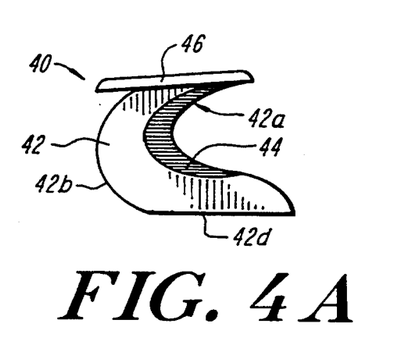
FIGS. 4A–4C are side elevational views of three embodiments of the cutting element.
Figure 4B:
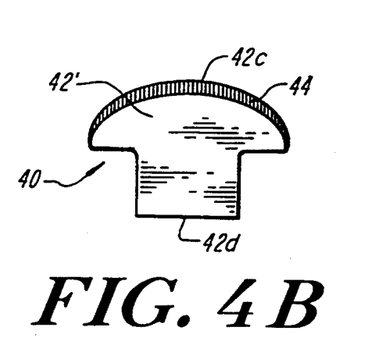
Figure 4C:
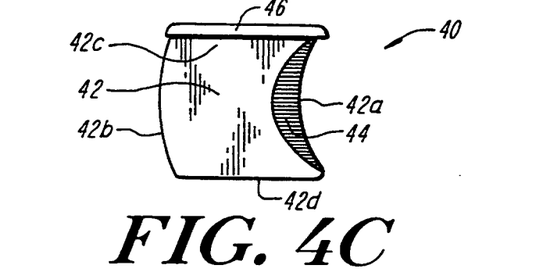

The cutting element 40 shown in FIGS. 4A through 4C is affixed to the distal end 30b of the actuating wire 30 and extends through the slot 24 in the arc portion 22 of the guide tube 20 in a plane transverse to the plane of the cutting trace 26. Various embodiments of the cutting element are desirable for performing various types of meniscal excisions on the various types of meniscal tears previously described. In a preferred embodiment, shown in FIG. 4A, the cutting element 40 comprises a curved or hooked blade 42 having leading edge 42a, trailing edge 42b, top edge 42c and bottom edge 42d. Leading edge 42a includes a sharpened cutting zone 44 on at least one side, and preferably both sides, of the hooked blade 42. The cutting zone 44 is oriented in a plane transverse to the plane of the cutting trace 26. As shown in FIG. 4A, leading edge 42a may have a curved, preferably concave, profile on which the cutting zone 44 is located. As shown in FIGS. 4A and 4C, trailing edge 42b may have a convex, straight or other profile. The hooked blade geometry illustrated in FIG. 4A is designed to catch and guide the meniscal tissue toward the center of the hooked blade 42 and the cutting zone 44 localized thereon, thereby reducing the risk of stray cuts and damage to surrounding tissue. The cutting element illustrated in FIG. 4A cuts in one direction only. However, the cutting element may be placed on the actuating wire facing either end of the arcuate cutting trace. The cutting element shown in FIG. 4C is more suitable for cutting meniscal tissue in the direction of the distal end of the cutting trace.

In other embodiments, either one of the leading edge 42a or the trailing edge 42b, or both, of the blade 42 may include a sharpened cutting zone. Cutting elements which have cutting zones on both leading and trailing surfaces are capable of cutting in both the clockwise and counter-clockwise directions. FIG. 4C shows another embodiment of the cutting element similar to that shown in FIG. 4A.

The cutting element 40 is preferably suitably dimensioned to enable the meniscectomy knife to be cleanly inserted into a portal of normal size and easily manipulated within the knee joint region without catching the surrounding tissue. Preferred dimensions for the hooked blade embodiment of the cutting element illustrated in FIG. 4A are a height of 0.10 inch to 0.15 inch, a thickness of 0.017 inch and a hook radius of 0.020 inch.

An alternative embodiment of the cutting blade, illustrated in FIG. 4B, includes a hemispherical blade 42' having a continuous cutting zone 44' on the top edge 42 and on at least one side, and preferably two sides, of the blade. This embodiment of the cutting element can cut tissue in either the clockwise or counter-clockwise direction. A preferred hemispherical blade has a diameter of 0.10 inch and a thickness of 0.017 inch.

The cutting element 40 is preferably made of a rigid material which is suitable for use in surgical environments. It is preferably honed to obtain a razorlike sharpness in a localized cutting zone and can be joined, such as by welding, to the distal end 30b of the actuating wire, to ensure that it does not break away from the meniscectomy knife during surgery. The cutting element is preferably joined to the actuating wire at the bottom edge 42d of the hooked cutting blade by a spot weld. However, any means known in the art for securing the cutting element to the actuating wire may be employed. Preferred materials for the cutting element include stainless steel, tungsten carbide, and alloys of vanadium, titanium and carbon steel.

The embodiments of the cutting element shown in FIGS. 4A and 4C additionally comprise a broadened flat skid 46 joined to the top edge 42c of the hooked cutting blade 42 and extending in a plane parallel to the plane of the cutting trace 26 and transverse to the plane of the cutting zone 44. The skid 46 is designed to facilitate the passage of the meniscectomy knife into and out of the meniscal region of the knee joint by shielding the surrounding tissue from the hooked blade 42 and the cutting zone 44 localized thereon. The skid also acts to channel the meniscal tissue toward the cutting zone on the leading edge 42a of the hooked blade as the cutting element is advanced through the meniscus.

Figure 9A:
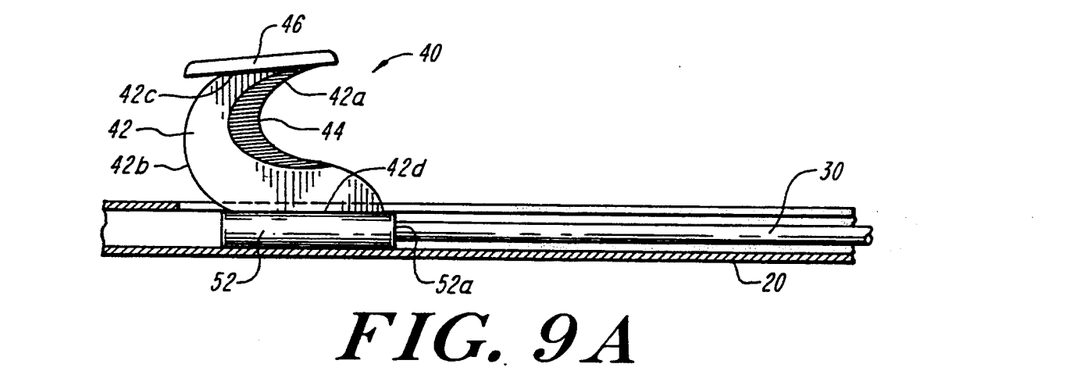
FIGS. 9A and 9B are longitudinal cutaway views of two embodiments of the cutting element mounted to the actuating wire disposed in the guide tube.
Figure 9B:
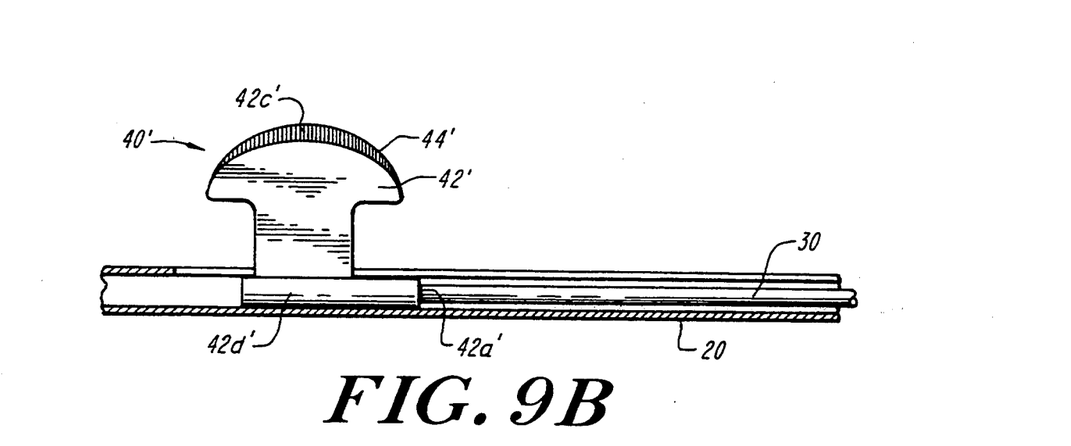

FIGS. 9A and 9B show hooked and hemispherical cutting elements 40 and 40' with hooked and hemispherical cutting zones 44 and 44', respectively, mounted onto the distal end of the actuating wire 30. In FIG. 9A, a welding block 52 has been welded to the bottom edge 42d of the cutting element 40 for purposes of attachment of the blade. The welding block is welded at its proximal edge 52a to the actuating wire 30. FIG. 9B similarly shows the hemispherical cutting element 40' welded directly to the actuating wire 30. The actuating wire and welding block are held within the guide tube 20 and the cutting element protrudes through the slot 24 (not shown).

Figure 5A:
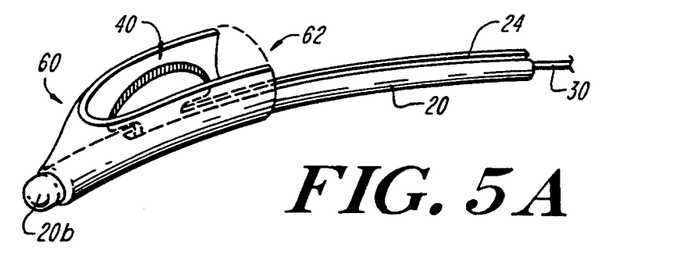
FIGS. 5A and 5B are side elevational views of two cutting element embodiments within a protective sheath located at the distal end of the guide tube.
Figure 5B:
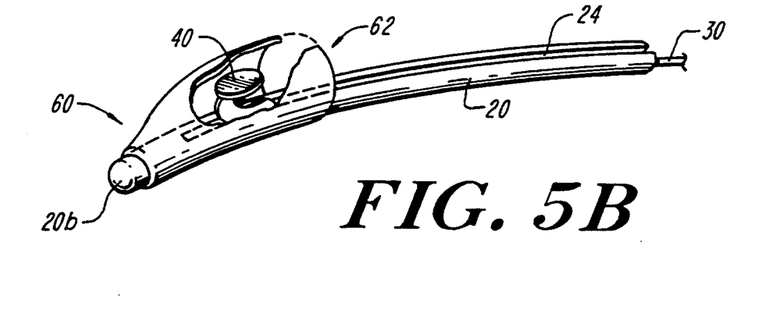

As shown in FIGS. 5A and 5B, the meniscectomy knife may further comprise a protective housing or sheath 60 which shields at least a portion of the cutting element 40 from surrounding tissue when the meniscectomy knife is being inserted into or withdrawn from the knee joint incision or not otherwise being engaged. The protective sheath 60 may be in the shape of an elongated receptacle having an open end 62 which receives the cutting element. It may be affixed, such as by a weld or other adhesive means, to either the distal or proximal end of the slot 24 such that the open end 62 faces the cutting element within the cutting trace 26 and receives the cutting element 40. It is preferably made of an inexpensive, easily formed material which is suitable for use in surgical environments and is compatible with the material used in the guide tube. Preferred materials include alloys of stainless steel, titanium and nickel. Preferred dimensions for the protective sheath are a height of 0.170 inch, a length of 0.250 inch and an opening width of 0.050 inch. The sheath 60 may be designed to at least partially surround or enclose the skid 46 as well as the cutting element 40, or it may be designed to enclose only the cutting element Other alterations to the above-described embodiments will be readily apparent to those ordinarily skilled in the art and are intended to be embraced within the spirit and scope of the invention. That is, the above description is intended to be illustrative rather than limiting. The invention is to be defined, therefore, not be the preceding description but by the claims that follow.

What is claimed is:

1. A meniscectomy knife comprising
a handle having distal and proximal ends and a handle axis,
a guide tube affixed to the distal end of the handle and extending away from the handle along the handle axis, at least a portion of the guide tube being preformed to include an arc portion defined by a cutting radius, the arc portion having a first surface and a slot extending along at least a portion thereof to define a cutting trace therein,
an actuating wire disposed within the guide tube and movable therethrough along a longitudinal axis thereof,
motion producing means disposed within said handle for imparting longitudinal motion to the actuating wire along the actuating wire axis, a proximal end of the actuating wire being affixed to said motion producing means such that activation of said motion producing means causes longitudinal movement of the actuating wire within the guide tube along the actuating wire axis, a distal end of the actuating wire moving along the arcuate path defined by the arc portion of the guide tube, and
a cutting element affixed to the distal end of the actuating wire and extending through the slot in the arc portion of the guide tube, the cutting element being movable along the cutting trace.

2. A meniscectomy knife comprising
a hollow handle having distal and proximal ends and a handle axis,
a retractable plunger disposed within the handle and movable therein along the handle axis,
a guide tube affixed to the distal end of the handle and extending away from the handle along the handle axis, at least a portion of the guide tube being preformed to include an arc portion defined by a cutting radius, the arc portion having a first surface and a slot extending along at least a portion thereof to define a cutting trace therein,
an actuating wire disposed within the guide tube and movable therethrough along a longitudinal axis thereof, a proximal end of the actuating wire being affixed to the distal end of the retractable plunger such that movement of the plunger along the handle axis causes longitudinal movement of the actuating wire within the guide tube along the actuating wire axis, a distal end of the actuating wire moving along the arcuate path defined by the arc portion of the guide tube, and
a cutting element affixed to the distal end of the actuating wire and extending through the slot in the arc portion of the guide tube, the cutting element being movable along the crating trace.

3. A meniscectomy knife comprising
a hollow handle having distal and proximal ends and a handle axis,
a guide tube affixed to the distal end of the handle and extending away from the handle along the handle axis, at least a portion of the guide tube being optionally preformed to include an offset portion defined by an offset distance from the handle axis and an arc portion defined by a cutting radius, the arc portion having a first surface and a slot extending along at least a portion thereof to define a cutting trace therein,
an actuating wire disposed within the guide tube and movable therethrough along a longitudinal axis thereof, motion producing means disposed within said handle for imparting longitudinal motion to the actuating wire along the actuating wire axis, a proximal end of the actuating wire being affixed to the motion producing means such that activation of the motion producing means causes longitudinal movement of the actuating wire within the guide tube along the actuating wire axis, a distal end of the actuating wire moving along the arcuate path defined by the arc portion of the guide tube, and a cutting element affixed to the distal end of the actuating wire and extending through the slot in the arc portion of the guide tube, the cutting element being movable along the cutting trace.

4. A meniscectomy knife comprising a hollow handle having distal and proximal ends and a handle axis, a retractable plunger disposed within the handle and movable therein along the handle axis, a guide tube affixed to the distal end of the handle and extending away from the handle along the handle axis, at least a portion of the guide tube being optionally preformed to include an offset portion defined by an offset distance from the handle axis and an arc portion defined by a cutting radius, the arc portion having a first surface and a slot extending along at least a portion thereof to define a cutting trace therein, an actuating wire disposed within the guide tube and movable therethrough along a longitudinal axis thereof, a proximal end of the actuating wire being affixed to the distal end of the retractable plunger such that movement of the plunger along the handle axis causes longitudinal movement of the actuating wire within the guide tube along the actuating wire axis, a distal end of the actuating wire moving along the arcuate path defined by the arc portion of the guide tube, and a cutting element affixed to the distal end of the actuating wire and extending through the slot in the arc portion of the guide tube, the cutting element being movable along the cutting trace.

5. A meniscectomy knife for use with a handle having a handle actuating member comprising:

a guide tube for affixing to the distal end of said handle, at least a portion of the guide tube being preformed to include an arc portion defined by a cutting radius, the arc portion having a first surface and a slot extending along at least a portion thereof to define a cutting trace therein, an actuating wire disposed within the guide tube and movable therethrough along a longitudinal axis thereof for affixing to said handle actuating member at the proximal end of said actuating wire, such that activation of said handle actuating member causes longitudinal movement of the actuating wire within the guide wire tube along the actuating wire axis, a distal end of the actuating wire moving along the arcuate path defined by the arc portion of the guide tube, and a cutting element affixed to the distal end of the actuating wire and extending through the slot in the arc portion of the guide tube, the cutting element being movable along the cutting trace.

6. A meniscectomy knife in accordance with claim 5, wherein at least a portion of said guide tube is preformed to include an offset portion defined by an offset distance from said longitudinal axis.

7. A meniscectomy knife according to claim 1, 2, 3, 4 or 5 further comprising a sheath affixed to the distal end of the guide tube adjacent to either the distal or proximal end of the slot for housing and protecting at least a portion of the cutting element.

8. A meniscectomy knife according to claim 1, 2, 3, 4 or 5 further comprising a reinforcing sleeve on a proximal portion of the guide tube.

9. A meniscectomy knife according to claim 1 or 3 wherein the motion producing means comprises a retractable plunger disposed within the handle and affixed to a proximal end of the actuating wire and being movable longitudinally therein along the handle axis to impart longitudinal motion to the actuating wire and arcuate motion to the cutting element.

10. A meniscectomy knife according to claim 1, 2, 3, 4 or 5 wherein the arc portion of the guide tube is constructed to fit within the periphery of the meniscal region of a human knee joint.

11. A meniscectomy knife according to claim 1, 2, 3, 4 or 5 wherein the cutting radius of the arc portion of the guide tube is approximately 0.25–0.75 inches.

12. A meniscectomy knife according to claim 11 wherein the cutting radius of the arc portion of the guide tube is approximately 0.5 inch.

13. A meniscectomy knife according to claim 1, 2, 3, 4 or 5 wherein the length of the cutting trace along the arc portion of the guide tube is approximately one-half to two inches.

14. A meniscectomy knife according to claim 13 wherein the length of the cutting trace along the arc portion of the guide tube is approximately one and one-half inches.

15. A meniscectomy knife according to claim 3, 4 or 6 wherein the offset portion of the guide tube is offset a distance of 0.25–0.70 inches to the right or left of the longitudinal axis.

16. A meniscectomy knife according to claim 15 wherein the offset portion of the guide tube is offset a distance of approximately 0.50 inches to the right or left of the longitudinal axis.

17. A meniscectomy knife according to claim 1, 2, 3, 4 or 5 wherein the cutting trace is defined by an arc measuring between 90° and 230°.

18. A meniscectomy knife according to claim 17 wherein the cutting trace is defined by an arc measuring between about 120° and about 180°.

19. A meniscectomy knife according to claim 1, 2, 3, 4 or 5 wherein the cutting element includes at least one of a leading cutting zone and a trailing cutting zone.

20. A meniscectomy knife according to claim 19 wherein the leading cutting zone is double-sided.

21. A meniscectomy knife according to claim 19 wherein the leading or trailing cutting zone has a concave profile.

22. A meniscectomy knife according to claim 1, 2, 3, 4 or 5 wherein the cutting element includes a broadened flat skid extending from an exposed edge of the cutting element in a plane transverse to the plane of the cutting zone and parallel to the plane of the cutting trace.

23. A meniscectomy knife according to claim 1, 2, 3, 4 or 5 wherein the cutting element moves through the cutting trace in the guide tube a distance which is proportional to the distance by which the motion producing means causes axial movement of the actuating wire within the guide tube.

24. A meniscectomy knife according to claim 1, 2, 3, 4 or 5 wherein the cutting element is formed of a material selected from the group consisting of alloys of stainless steel, titanium, vanadium and carbon steel.

25. A meniscectomy knife according to claim 1, 2, 3, 4 or 5 wherein the actuating wire is formed of stainless steel.

26. A meniscectomy knife according to claim 1, 2, 3 or 4 wherein the handle is made of a rigid polymeric material.

27. A meniscectomy knife according to claim 2 or 4 wherein the handle and plunger are made of a rigid polymeric material.

28. A meniscectomy knife according to claim 1 or 3 wherein the guide tube, actuating wire and cutting element are removable from the handle and the motion producing means.

29. A meniscectomy knife according to claim 2 or 4 wherein the guide tube, actuating wire and cutting element are removable from the handle and the plunger.

* * * * *